US011484709B2

(12) United States Patent
Verity (10) Patent No.: US 11,484,709 B2
(45) Date of Patent: Nov. 1, 2022

(54) APPARATUS FOR NEUROMUSCULAR STIMULATION

(71) Applicant: Nigel Charles Verity, Hampshire (GB)

(72) Inventor: Nigel Charles Verity, Hampshire (GB)

( * ) Notice: Subject to any disclaimer, the term of this patent is extended or adjusted under 35 U.S.C. 154(b) by 246 days.

(21) Appl. No.: 16/618,034

(22) PCT Filed: May 31, 2018

(86) PCT No.: PCT/GB2018/051479
§ 371 (c)(1),
(2) Date: Nov. 27, 2019

(87) PCT Pub. No.: WO2018/220374
PCT Pub. Date: Dec. 6, 2018

(65) Prior Publication Data
US 2020/0139115 A1 May 7, 2020

(30) Foreign Application Priority Data
May 31, 2017 (GB) ..................... 1708654

(51) Int. Cl.
*A61N 1/36* (2006.01)
*A61N 1/04* (2006.01)
(52) U.S. Cl.
CPC ....... *A61N 1/36003* (2013.01); *A61N 1/0452* (2013.01); *A61N 1/36007* (2013.01)
(58) Field of Classification Search
CPC .............. A61N 1/36003; A61N 1/0452; A61N 1/36007
See application file for complete search history.

(56) References Cited

U.S. PATENT DOCUMENTS 4,582,049 A 4/1986 Ylvisaker
4,785,813 A 11/1988 Petrofsky
(Continued)

FOREIGN PATENT DOCUMENTS

CN 202654544 U 1/2013

OTHER PUBLICATIONS

Saxena et al., "An EMG-controlled grasping system for tetraplegics," Journal of Rehabilitation and Development, vol. 32, No. 1, (Feb. 1995), pp. 17-24.
(Continued)

*Primary Examiner* — Mark W. Bockelman (57) ABSTRACT

The present invention relates to an apparatus and a method for neuromuscular stimulation which is useful for stimulation of weak muscles in general, in sports clinical mode for muscle growth and endurance and in clinical mode for muscular rehabilitation. EMG signals are received from the subject adjacent a muscle whose contraction is to be stimulated. A succession of stimulation (STIM) pulses are supplied to the muscle to be stimulated. The EMG-receiving module is operated during quiescent periods between successive pulses, and the amplitude of stimulation pulses supplied to the subject in the succession is modulated proportionately depending on the a detected voluntary component of the received EMG signals. Modulation is in real time during supply of stimulation pulses whereby the subject is given a sensation of natural muscle control and/or the possibility for greater precision of neuromuscular control.

15 Claims, 5 Drawing Sheets

(56) References Cited

U.S. PATENT DOCUMENTS

| | | | |
|---|---|---|---|
| 5,092,329 A | 3/1992 | Graupe et al. | |
| 10,537,733 B2* | 1/2020 | Dixon | A61N 1/36031 |
| 2003/0208246 A1 | 11/2003 | Kotlik et al. | |
| 2008/0234781 A1 | 9/2008 | Einav | |
| 2013/0296746 A1* | 11/2013 | Herr | A63B 21/00181 |
| | | | 601/34 |
| 2014/0277309 A1 | 9/2014 | Popovic | |
| 2015/0217120 A1 | 8/2015 | Nandra | |

OTHER PUBLICATIONS

Quandt et al., "The influence of functional electrical stimulation on hand motor recovery in stroke patients: a review." Experimental & translational stroke medicine, vol. 6:9. (Aug. 21, 2014).

Liberson et al., "Functional electrotherapy: stimulation of the peroneal nerve synchronized with the swing phase of the gait of hemiplegic patients," Archives of Physical Medicine and Rehabilitation, No. 42, (Feb. 1961), pp. 101-105.

International Search Report for PCT/GB2018/051479.

Abstract for CN 202654544.

Muraoka, Y., "Specifications of an electromyogram-driven neuromuscular stimulator for upper limb functional recovery," Engineering in Medicine and Biology Society (EMBC), 2013 35th Ann. International Conference of the IEEE, Jul. 3, 2013, (ISSN: 1557-170X), pp. 277-280. (Please Refer To ISR).

Francisco G., et al., "Electromyogram-triggered neuromuscular stimulation for improving the arm function of acute stroke survivors: A randomized pilot study," Archives of Physical Medicine and Rehabilitation, pub. by W.B. Saunders, vol. 79, No. 5, May 1, 1998, pp. 570-575 (ISSN: 0003-9993) (Please Refer To ISR).

\* cited by examiner

Electrically (FES) facilitated or assisted voluntary muscle contraction by means of voluntary EMG detected during the interpulse intervals of FES within the composite EMG which is overwhelmingly dominated by the m-wave by means of subtraction of the next m-wave model predicted and synthesized using a recursive self-adapting neutral network algorithm.

APPARATUS FOR NEUROMUSCULAR STIMULATION

FIELD OF THE INVENTION

The present invention relates to an apparatus and a method for neuromuscular stimulation which is useful for stimulation of weak muscles in general, in sports clinical mode for muscle growth and endurance and in clinical mode for muscular rehabilitation in subjects suffering e.g. from stroke, paresis, cerebral palsy, incontinence and muscle atrophy. The process also provides enhancement of the force of a voluntary muscle contraction by a train of electrical pulses whose instantaneous amplitude is controlled by the intensity of the on-going effort of contraction of that muscle, in real time, pulse by pulse though out the onset, maintenance and release phases of that contraction.

BACKGROUND TO THE INVENTION

Electrical pulses have been used for many years for muscle stimulation. For example, U.S. Pat. No. 5,092,329 (Graupe et al.) explains in its background section that work on functional electrical stimulation of paraplegics is based on the discovery of the Italian physiologist Luigi Galvani in the late 18th century that a muscle will contract when in contact with an electrical charge. This was said to have been first applied systematically to paralyzed patients by W. Liberson et al., *Arch. Phys. Med. Rehab.*, Vol. 42, p. 101, (1961). Application of trains of pulses of adequate amplitude, pulse-width and pulse-repetition-frequency at appropriate locations above the region of certain key muscles enabled paraplegic patients with complete or near-complete upper-motor-neuron lesions to stand up and to take steps with the support of parallel bars or a walker. Stimulation parameters for successful functional electrical stimulation (FES) have been said to be of frequency: 20-50 Hz, pulse width: 30-500 μs and amplitude ≤100 mA, see Quandt et al., *Exp Transl Stroke Med.* 2014; 6: 9. This is an involuntary muscular response out of the control of the patient. Such electrical stimulation has been shown to produce muscle response even in dead bodies for several hours after death.

Electromyography (EMG) is an electro-diagnostic medical technique for evaluating and recording the electrical activity produced by skeletal muscles. EMG is performed using an electromyograph to produce a record called an electromyogram. An electromyograph detects the electrical potential generated by muscle cells when these cells are electrically or neurologically activated. Evoked (involuntary) EMG signals comprise a combination that can include M, H, F and E waves each one with a different characteristic and latency, and the signals can be analysed to detect medical abnormalities, activation level, or recruitment order or to analyse the biomechanics of human or animal movement. As the amplitude of an individual pulse increases from zero to the point where the muscle just starts to engage with mechanical force (perhaps about 10 mA) an evoked EMG (m wave etc.) will appear and its amplitude start to increase from a low level up to perhaps as much or even more than 10 millivolts as the FES pulse amplitude is increased to the point where the muscle is exhibiting maximal contraction. A single pulse of FES will cause a single pulse of muscular contraction to occur with its peak a few milliseconds after the pulse. However, if a train of pulses are applied to the muscle with small enough delay between one pulse and the next (for example 40 mS) then what appears to be a sustained mechanical contraction of the muscle will result. The evoked EMG between each pulse and the next has been measured and used to control and regulate the electrical stimulator for improved results. In EMG biofeedback, surface electrodes or vaginal/anal probe are used to record the electrical activity in a muscle or muscle group at rest and during contraction. EMG biofeedback is used both for diagnosis and as a therapy to provide the patient and the therapist with information about the electrical activity in the muscles. This method provides extra feedback when the natural feedback signals of the patient are insufficient to achieve the contraction. In other words, it supplements the physiological feedback. This method is especially useful in the case of muscular activity that produces a contraction or movement that is invisible to the patient. An example is to be found in the muscles of the pelvic floor and anus. Myofeedback provides extra information for the motor learning process. The electromyographic signal (EM signal=the electrical resultant of the neuromuscular activity) is detected both in a contraction and in the exclusively electrical activity of a muscle when there is no discernible muscle activity. Therefore, it allows the patient to realize that he or she has control over the activity of their muscles, even if it is very small, or in the case of complete paralysis provides a view on how much it increases during therapy. In addition, the EMG biofeedback allows learning control of muscle contraction, using specialized equipment amplifying the signal received from the muscles. Together with appropriate software and configuration this allows visualization of muscle activity on a computer or other screen in real time. A patient on a regular basis can correct muscle contractile activity, seeing on an electronic display what he or she is not able to feel.

FES such as, for example, that used for "foot drop", can be triggered by a button press. Alternatively, voluntary EMG arising from a typically inadequate voluntary contraction can be used to trigger the onset of a period of useful electrically driven muscular contraction such as that needed, in this example, just long enough to keep the front of the foot up for a sufficient time to complete the step. In both cases the time period of the electrical stimulation and its intensity is predetermined and pre-set to achieve the desired functional result.

EMG-triggered FES links voluntary movement attempts to electrical stimulation, see Quandt et al., supra. An assessment was reported of the efficacy of electromyogram (EMG)-triggered neuromuscular stimulation (EMG-stim) in enhancing upper extremity motor and functional recovery of acute stroke survivors, see Francisco G et al., Electromyogram-triggered neuromuscular stimulation for improving the arm function of acute stroke survivors: a randomised pilot study, *Arch Phys Med Rehabil*, 79:5 570-5, (1998). EMG signal from the paretic muscle was rectified and integrated. If the processed signal exceeded the pre-set threshold (a minimum of 5 μV), an Automove stimulator (Krauth & Timmerman, GmbH) generated a 0.2 msec width, 0 to 60 mA, biphasic square wave pulse at 20 to 100 Hz. The duty cycle was set for 5 seconds on and 5 seconds off. The EMG detector sensitivity ranged between 5 and 80 μV. The "all or none" stimulus was set for maximum range of motion, not torque. Frequency was adjusted to subject comfort. The skin was examined before and after each session for burns and skin breakdown. Stimulus threshold was gradually increased with each session as voluntary recruitment increased. It was concluded that EMG-triggered stim enhanced the arm function of acute stroke survivors. An EMG-controlled (i.e. triggered) grasping system for tetraplegics is described by Saxena, Nikolic and Popovic, *J Rehabil Res & Develop,*

32:17-24, 1995. The control signal that turned the stimulation of forearm finger and thumb flexors on and off was based on the detection of the threshold of the amplified, rectified, and integrated electromyographic recordings using surface electrodes positioned over the wrist extensors. The voluntary contraction of wrist extensors was suitable for triggering the stimulation, and it was reproducible enough for daily home use. It was possible to use very similar parameters of stimulation in all subjects: T=200 µs, f=20 Hz, I=35 mA, monophasic charged compensated pulses. The patient selected the level of stimulation using video or audio feedback during stimulation while performing routine activities. The designed device worked using an on-off controller, and there was no gradation in the force.

SUMMARY OF THE INVENTION

The invention provides apparatus and a process for real time proportional voluntary EMG control of neuromuscular electrical stimulation (PECS) by means of continuous detection of the voluntary component of the EMG from the voluntary contraction of that same muscle during the stimulation. Embodiments of the invention provide electro-facilitated voluntary muscle stimulation in real time.

In an embodiment, the invention provides apparatus for neuromuscular stimulation, comprising:

(a) a module for receiving EMG signals from skin adjacent a muscle whose contraction is to be stimulated;

(b) a module for supplying a succession of stimulation pulses to the muscle; and (c) a controller configured to cause the EMG-receiving module to be operable during quiescent periods between successive pulses and to modulate the amplitude of stimulation pulses in the succession depending on the voluntary component of the received EMG signals.

Detection of the voluntary component may involve averaging detected m-wave pulses in periods between successive stimulation pulses to derive predicted m-wave profiles and for successive m-waves determining differences between detected and predicted m-wave values of period less than that of the m-wave and corresponding to said voluntary component.

In embodiments, the module for receiving the voluntary EMG signals outputs to the controller the value of the voluntary EMG signals above a predetermined threshold. The module for receiving EMG signals may be operative between only some of the pulses in the succession but preferably is operative between each pair of successive pulses, and in further preferred embodiments it is operative substantially continuously between each pair of successive pulses. The controller may be configured to average the detected voluntary EMG signals to smooth amplitude modulation, whereby a user can achieve smooth volume controlled muscle contraction The STIM pulses are preferably symmetrical bipolar square-wave pulses and have phase duration which is short compared to the inter-pulse interval and the controller may be configured so that the STIM pulses do not exceed a maximum amplitude even on prolonged high values of the voluntary EMG signal. Circuits forming part of the apparatus may be configured to reduce DC voltage at the electrodes during the inter-pulse interval and avoid swamping of the composite EMG signal.

In a further embodiment, the invention provides a method for producing neuromuscular stimulation pulses, comprising:

(a) receiving EMG signals from skin adjacent a muscle whose contraction is to be stimulated;

(b) supplying a succession of stimulation (STIM) pulses;

(c) operating the EMG-receiving module during quiescent periods between successive pulses; and (d) modulating the amplitude of stimulation pulses in the succession depending on the detected voluntary component of the received EMG signals.

In a yet further embodiment the invention provides a method for supplying neuromuscular stimulation pulses to a subject, comprising:

(a) receiving EMG signals from the subject adjacent a muscle whose contraction is to be stimulated;

(b) supplying a succession of stimulation (STIM) pulses to the muscle to be stimulated;

(c) operating the EMG-receiving module during quiescent periods between successive pulses; and (d) modulating the amplitude of stimulation pulses supplied to the subject in the succession depending on the received EMG signals.

The EMG signals and the STIM pulses may be received and supplied through the same pair of electrodes, or the EMG signals may be received through a first pair of electrodes and the STIM pulses may be supplied through a second pair of electrodes. In either case the EMG signals are preferably received and the STIM pulses are preferably supplied through skin electrodes, although the use of other forms of electrode e.g. inserted fine wire electrodes is also possible. Modulation is in real time during supply of stimulation pulses whereby the subject is given a sensation of natural muscle control and/or the possibility for greater precision of neuromuscular control. By modulating the STIM pulses also with knowledge of limb position, it is believed that better stability and more precise control may be achievable using MEM or other control signals.

The EMG signals in the case of a contracting muscle may appear as a modulation on inter STIM-pulse M-waves, both the EMG signals and the M-waves being sensed as a composite EMG signal and the controller being configured to detect M-wave latency and/or amplitude. The apparatus may further comprise a display, and the controller may be configured to output to the display STIM-pulse voltage, EMG-voltage and M-wave latency as a function of STIM-pulse voltage and/or EMG characteristics e.g. positive amplitude and/or latency.

Embodiments of the device are battery powered and hand held but can also be mains electrically driven free standing devices.

BRIEF DESCRIPTION OF THE DRAWINGS

An embodiment if the invention will now be described with reference to the accompanying drawings, in which.

DETAILED DESCRIPTION OF PREFERRED EMBODIMENTS

Figure 1:
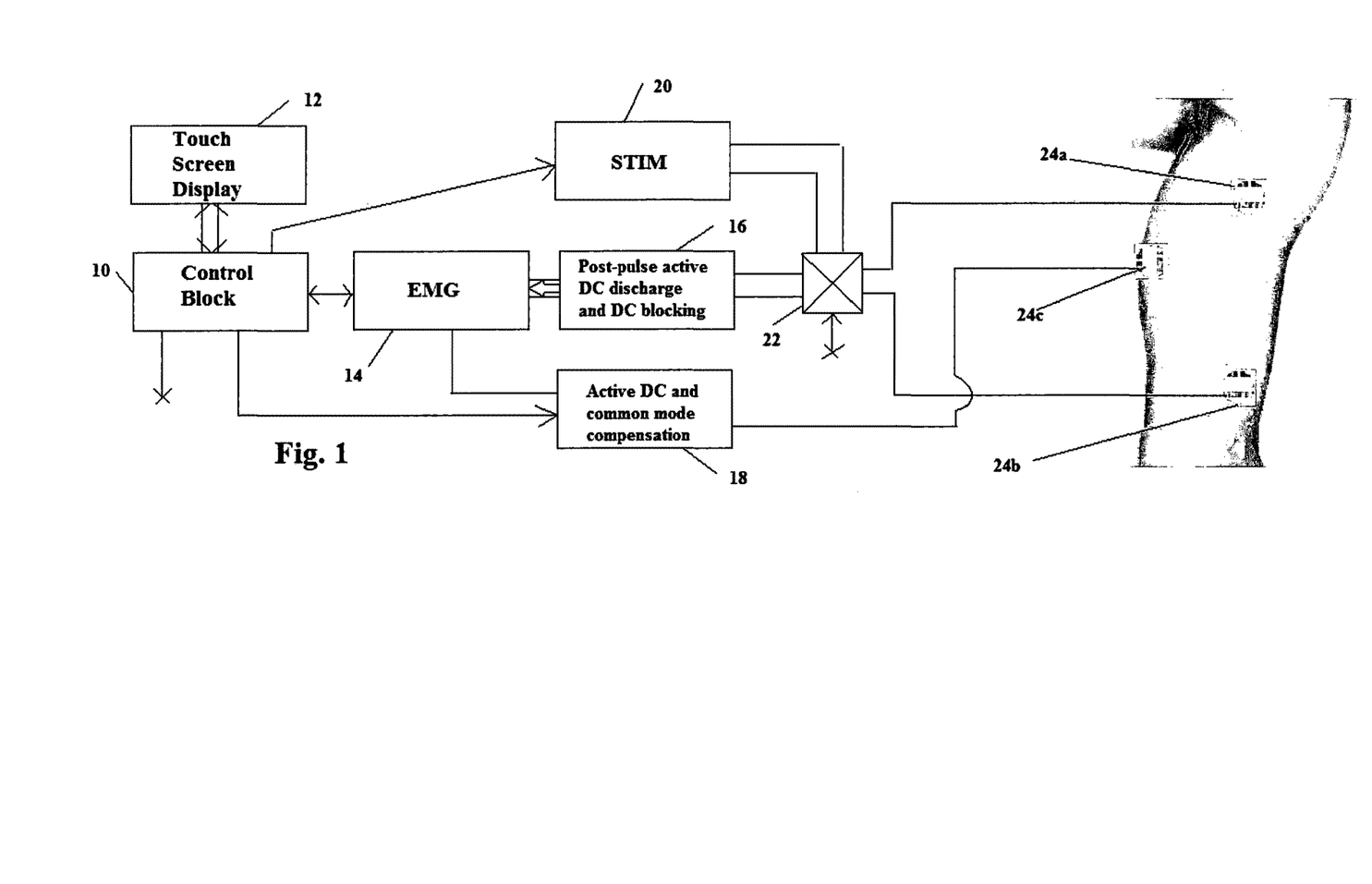
FIG. 1 is a block diagram of apparatus according to a first embodiment of the invention for detecting the voluntary component of the composite EMG and delivering a trail of neuromuscular stimulation pulses having amplitude determined by the voluntary EMG level determined in the intervals between pulses.

In FIG. 1, apparatus for delivering real time voluntary EMS controlled stimulation pulse train amplitude comprises a control block 10 in bidirectional communication with a touch screen display 12 and optionally with a keyboard (not shown).

Operation of stimulation module 20 is controlled via control block 10. In the illustrated embodiment STIM block 20 which is a single channel stimulator is configured to deliver a symmetrical rectangular biphasic waveform with net zero DC current. Constant current maximum voltage output may be in the range 0-70V, giving pulse amplitudes of 0-90 mA into a 500Ω load, although the actual mA may be less than this owing to electrode impedance, a load of 1000Ω giving a maximum current of 75 mA and a 1500Ω load giving a maximum current of 50 mA. Phase durations in each pulse may be from 50-450 e.g. 50-330 µS±10% e.g. 300 µS and the pulse repetition rate may typically be 2-100 Hz±10%. Circuitry and software to generate pulses of this type is known and is incorporated, for example, in stimulators in the Verity Medical Neurotrac range. It will be appreciated that the device may have more than one stimulation channel, e.g. two, three or four stimulation channels or more, in which case there will be a corresponding number of additional STIM blocks 20. Four stimulation channels may be advantageous e.g. for sequential arm movement. It will be appreciated that even at the highest pulse frequency of 100 Hz there is a quiescent period of 10 mS between each pair of pulses, and the pulse duration of only e.g. ~1 mS for ~500 µS phase duration is small compared to the duration of the quiescent period. If the pulse repetition rate is 40 pulses per second then the inter-pulse interval is 25 mS. It will be appreciated that the quiescent period between pulses refers to events during the periods when stimulation is intended to be carried out (i.e. a muscle is being caused to contract) and is distinct from the duration of the work/rest stimulation cycles for the muscles of the user to be stimulated by the apparatus. The output of STIM block 20 is fed to optically controlled high-speed switch network 22 which may be a photoMOS or other switch and effects change-over between EMG and STIM operation. The precise switch type is not critical provided that the switch selected has adequate switching speed and provides adequate isolation between switched channels. Muscle stimulation electrodes 24a, 24b are connected by leads to the output of the switch network 22. The electrodes may be skin adhesive which is more convenient for general non-hospital use e.g. compared to surgically implanted electrodes. They may have a cloth backing and a water-based hydrogel and conductive carbon film and may be circular with diameter in the range 25-50 mm or square or rectangular e.g. of size 50×50 mm.

EMG block 14 is in bidirectional communication with control block 10. In the embodiment shown there is a single channel EMG block for a single muscle, but multichannel EMG may also be employed, e.g. two, three or four channels or even more, in which case there will be additional blocks corresponding to the block 14. Electrodes 24a, 24b are connected with EMG block 14 via switch network 22 and post-pulse active DC discharge and DC blocking module 16. An EMG reference electrode 24c is connected to active DC and common mode compensation block 18 which is in turn connected to control block 10 and EMG block 14. In the quiescent period between STIM pulses, the blocks 16, 18 serve to reduce residual voltage from the STIM pulses to a sufficiently low value to avoid swamping EMG signals from electrodes 24a, 24b during that period. Voluntary EMG signal voltages are substantially lower than the voltage applied by STIM pulses, being typically in the range 0.2-2000 µV, e.g. 10-500 µV and for many patients with real time values in the range 2-20 µV. The EMG block 14 and associated blocks may contain filters to block 50 or 60 Hz mains frequencies, and it may be inadvisable to use the present apparatus within 4 metres of a cellular telephone or near any other powerful radio interference producing equipment. EMG pulse frequencies at skin surface electrodes are typically ~120 Hz and following the Nyquist-Shannon sampling criterion are usually sampled at a rate at least 4-5 times the highest frequency component expected to be present in the EMG signal, conveniently at a rate of 1-2.5 kHz, e.g. ~2 kHz. In practice, to be indicative of user intention to contract a muscle, signal in an EMG channel should be above a threshold e.g. 10 µV (a relaxed muscle typically reading below 3.5 µV), the value being dependent upon muscle strength and user capabilities and pre-existing conditions e.g. stroke or paresis, and that threshold can be adjusted by user or clinician input via +/−keys either on touchscreen display 12 or on a separate keyboard.

Figure 2:
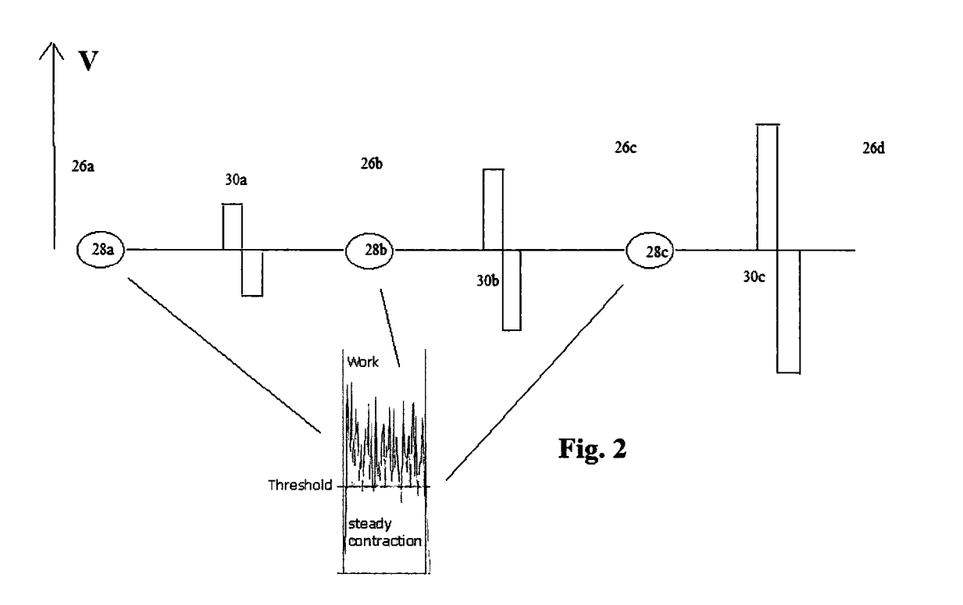
FIG. 2 is a diagram showing detected voluntary EMG above a threshold level and a train of progressively increasing pulses.
Figure 3:
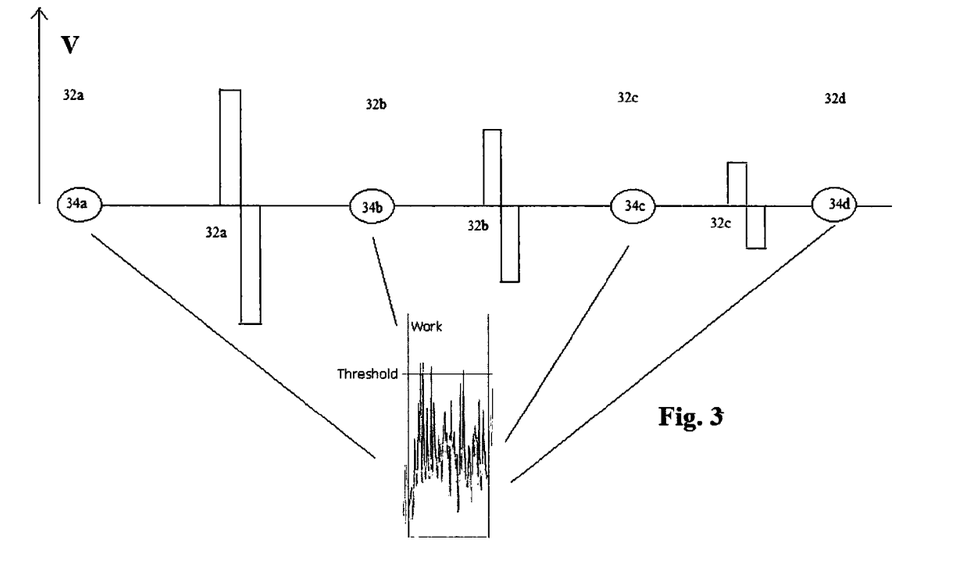
FIG. 3 is a diagram showing detected voluntary EMG below a threshold level and a train of progressively decreasing pulses.
Figure 4:
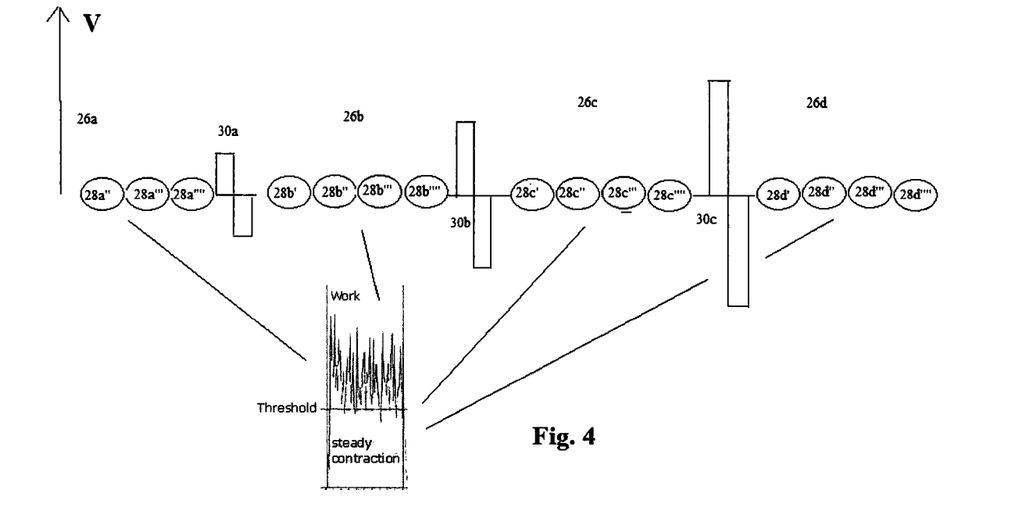
FIG. 4 is a diagram similar to FIG. 2 but showing multiple intervals of EMG detection between successive stimulation pulses.

According to the invention, EMG is sampled in the intervals between STIM pulses, and sampled values are used to modulate the values of subsequent stimulation pulses. Thus, in FIGS. 2,3, composite EMG sampling takes place during quiescent periods 26a-26 and in the example shown the detected voluntary EMG is significantly above a pre-set threshold, indicating that the user is making an effort to contract their muscle. In consequence, the STIM module 20 delivers pulses 30a-30c of progressively increasing amplitude in direct real time proportion to their effort. When they relax this effort in the opposite situation where samples taken during quiescent periods 32a-32d indicate reduced effort the STIM module delivers pulses of decreasing amplitude and zero amplitude if and when the effort falls below the pre-set threshold. It will be appreciated that it is not necessary to sample EMG between each pair of pulses, and only a proportion of quiescent periods may be sampled e.g. every two, every three or every four pulses. The resulting voluntary EMG modulation data may be averaged over several inter-pulse periods as appropriate to the condition of the user to bring about a smooth controlled muscle movement.

In use, the stimulation electrodes 24a, 24b are adhered to the skin above a specific muscle in the best position for good effect (knowledge of anatomy is helpful for this). The user is then asked to make their best efforts for a maximal (voluntary) contraction of the muscle in the absence of any electrical stimulation pulses during which time the EMG from these electrodes (which consists almost entirely of the voluntary EMG component) is measured such that the maximum and minimum reading of EMG readily achieved, is noted. The muscle is then stimulated via module 20 with these same electrodes to achieve a maximal comfortable contraction such that the device retains this value of stimulation current (mA). A maximum time for the stimulation may then be set e.g. to 5 seconds with an and the intervening period e.g. 10 seconds. The device is then switched to PECS stimulation mode and a start key is pressed. If the maximum comfortable stimulation current was found to be 30 mA, the minimum EMG achieved to be 4 microvolts and the maximum 15 microvolts rms, then in in proportional or PECS mode the device would function as follows. With the patient relaxed below 4 microvolts EMG there would be no stimulation. As the patient's voluntary contraction increased about 4 microvolts EMG the stimulation would start from zero mA linearly (or otherwise depending on the setting selected) such that at a level of 15 microvolts the maximum stimulation pulses of 30 mA would be achieved. As soon as the patient relaxed their voluntary contraction below 15 microvolts the stimulation would (immediately) proportionally reduce until it stopped altogether when they relaxed to below 4 microvolts. Or, if the time of the stimulation reached 5 seconds the stimulation would stop and the 10 seconds pre-set rest period would begin. During this rest period, any contraction above 4 microvolts would not result in stimulation in order to prevent over stimulation. PECS would only be re-enabled at the end to the rest period. In this way, the signals in the motor neurones of the user are complemented by a powerful stimulation signal which is proportional to voluntary EMG signal level above the pre-set threshold, and the patient is given a sensation of full muscular control rather than a mechanical-seeming on/off signal. It is believed that the resulting sensations of control will enhance the learning process needed for recovery or increased muscle power, and both recovery/enhancement time will be reduced and the extent of recovery/enhancement will be increased.

Referring now to FIGS. 5-8, voluntary EMG is the EMG measured at a muscle site when a patient makes an effort to contract that muscle generally by necessity for its detection at a time when no electrical stimulation pulses are being applied. It typically ranges between 0.4 and 100 microvolts in a patient that requires neuromuscular rehabilitation. In a weak person such as, for example, a stroke patient it may only reach a maximum of about 10 microvolts for a particular muscle site. This amplitude is 2 to 3 orders of magnitude lower than the amplitude of the potential maximal m-wave for that muscle [m wave 10 mV versus voluntary EMG 0.01 mV (10 microvolt)].

Voluntary EMG used to trigger a preprogramed, FES-driven muscle contraction can do this as it is invariably detected at the muscle site when no FES is being applied. [FES is 6 to 7 orders of magnitude higher than the Voluntary EMG typically used to trigger it]. The moment patients reach the necessary level of effort to trigger a FES contraction cycle, they normally relax their effort and passively let the electrical pulses complete the muscular contraction cycle. This muscle contraction cycle typically consists of a train of at least 20 pulses per second lasting no more than about 5 seconds after which the muscle under treatment relaxes for at least 5 seconds before the patient is once again asked to make a new effort to try to trigger another cycle. This process is continued for perhaps 10 to 20 cycles for the treatment session to be complete.

As discussed, it is very difficult to measure even the evoked (involuntary) EMG (m-waves) between each succeeding pulse of FES mostly because they are 2 to 3 orders of magnitude smaller than the FES pulses. And, voluntary EMG if present between pulses of FES close enough together to sustain a useful muscle contraction would be typically 2 to 3 orders of magnitude smaller than even the m-waves. The question arises whether if patients continue to make an effort to contract their muscle during its contraction, increased and sustained by electrical pulses, in these circumstances their voluntary EMG signal would be present, perhaps detectable as a small, apparent perturbation (tiny amplitude and phase modulation) of the generally ten thousand times larger m-wave? The literature appears to be entirely silent on this subject.

Surprisingly, it has been discovered by means of some of the methods and processes described below that the voluntary effort of the patient is indeed present in the form of a tiny but, nonetheless reliably detectable real time modulation of the (involuntary) m-wave as and when and only for the time that the patient makes their own effort to compliment the FES driven contraction with an amplitude roughly proportional to the intensity of that effort.

Figure 5:
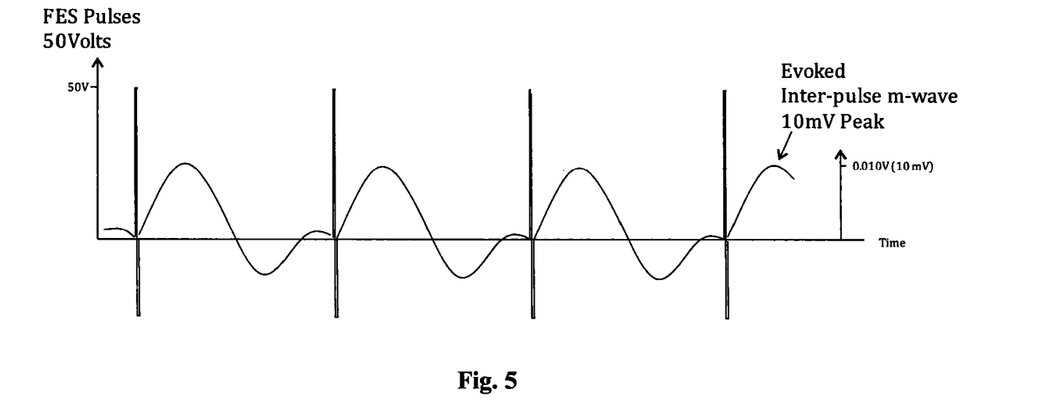
FIG. 5 is a diagram showing a sequence of stimulation pulses (volts) and evoked inter-pulse m-waves (millivolts)
Figure 6:
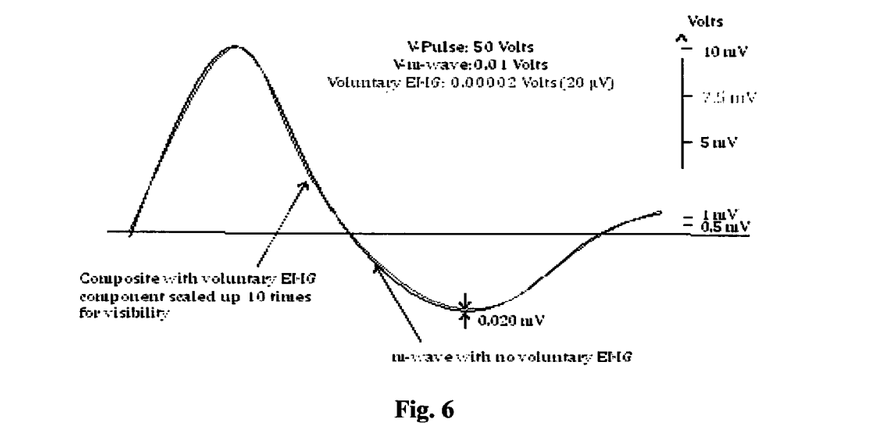
FIG. 6 is a diagram showing as one curve a single evoked inter-pulse m-wave with no voluntary EMG, and as a second curve a composite of the evoked m-wave with a voluntary EMG component shown scaled-up ten times for visibility.

FIG. 5 shows a series of FES pulses plotted against time between four successive pulses spaced at 25 milliseconds with the maximal m-waves as they appear between the pulses with no voluntary EMG present. with The pulses are drawn to a scale of volts, and the m-waves are drawn to a scale of mV (FES pulse width 300 μS, 40 pulses per second, amplitude 100 volts peak to peak). FIG. 6 shows one such m-wave on a larger scale. In the composite EMG measured during the inter-pulse intervals of effective muscle contractions sustained by FES the voluntary EMG is 2 to 3 orders of magnitude smaller than the involuntary component (m-waves). Each half-cycle of the voluntary EMG component has a variable period and amplitude. A composite of such an inter-pulse EMG wave containing both the m-wave component and voluntary EMG component (shown with the voluntary component scaled up ten times) is almost indistinguishable from one containing the m-wave component alone. That highlights the tiny effect on the composite signal caused by the voluntary effort of a typical weak patient during the FES cycle and therefore the difficulty in both its detection and quantification.

Figure 7:
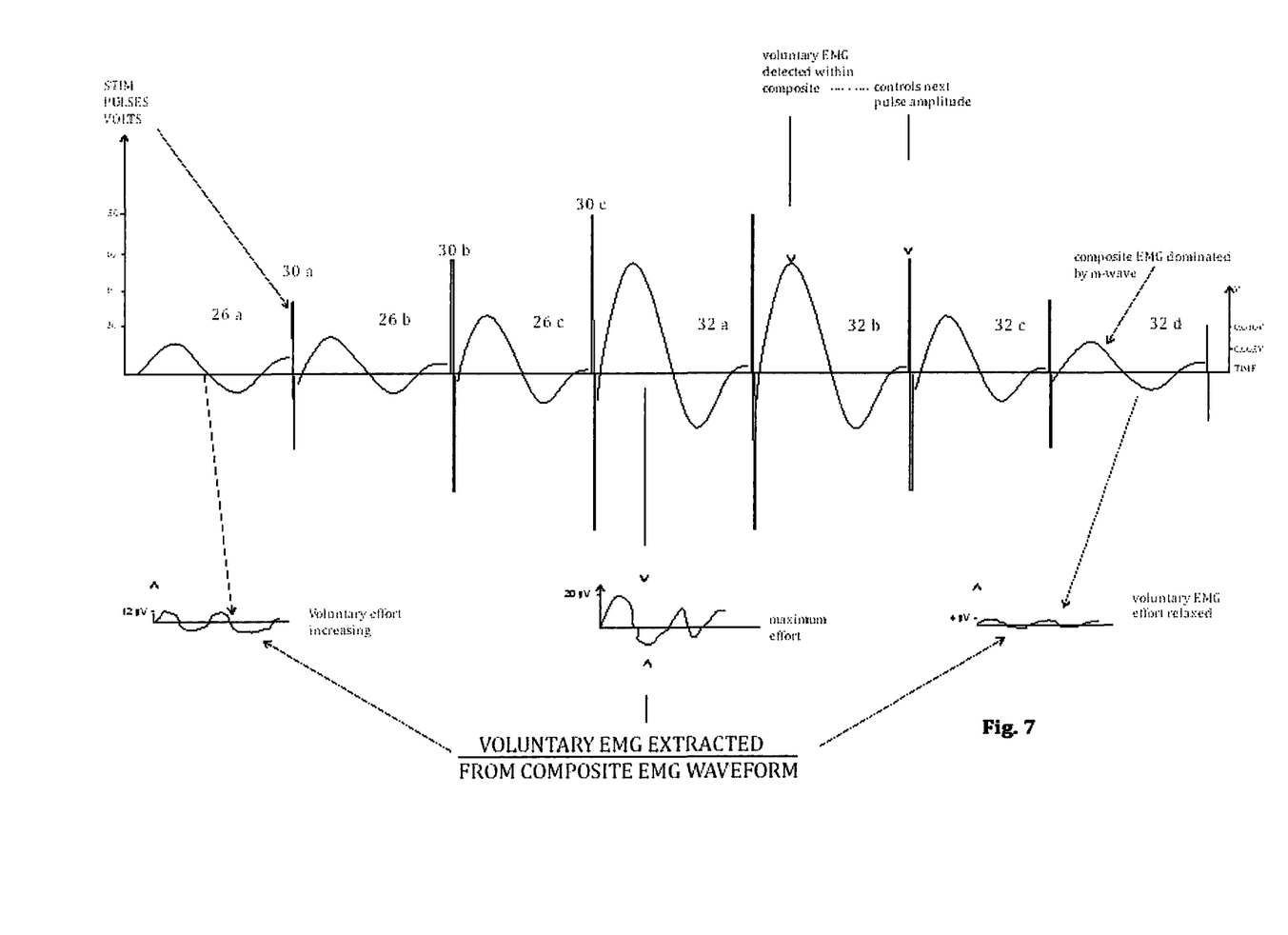
FIG. 7 is a diagram showing voluntary EMG detected between pulses increasing above the pre-set threshold and then decreasing towards it and the resulting train of proportionally increasing pulses and decreasing pulses controlled by it, pulse by pulse.

In FIG. 7, composite EMG sampling takes place during quiescent periods and in the example shown the detected voluntary EMG is significantly above a pre-set threshold, indicating that the user is making an effort to contract their muscle. In consequence, a STIM module delivers pulses of progressively increasing amplitude in direct real time proportion to their effort. When they relax this effort in the opposite situation where samples taken during quiescent periods indicate reduced effort the STIM module delivers pulses of decreasing amplitude and zero amplitude if and when the effort falls below the pre-set threshold. It will be appreciated that it is not necessary to sample EMG between each pair of pulses, and only a proportion of quiescent periods may be sampled e.g. every two, every three or every four pulses. The resulting voluntary EMG modulation data may be averaged over several inter-pulse periods as appropriate to the condition of the user to bring about a smooth controlled muscle movement.

Figure 8:
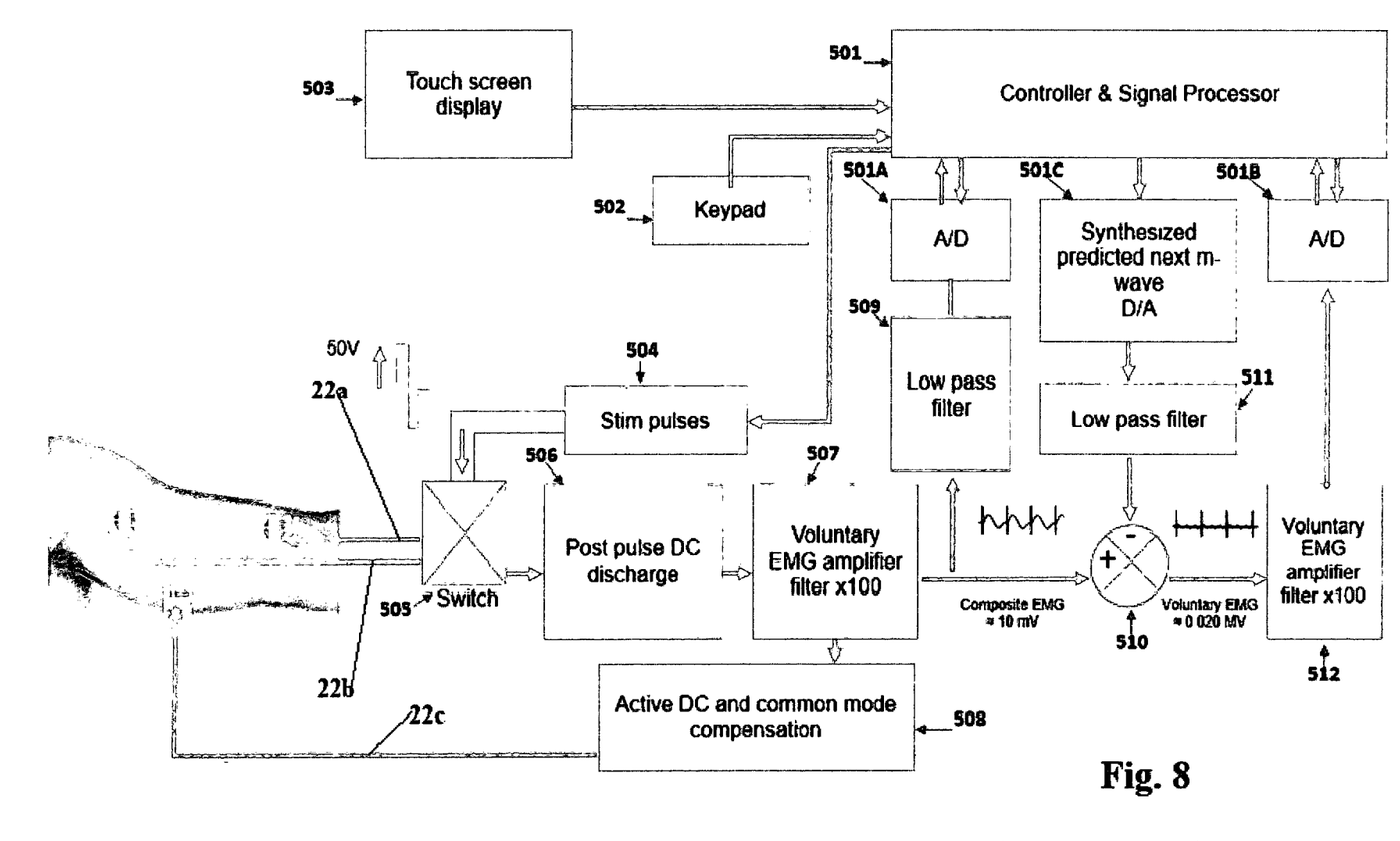
FIG. 8 is a block diagram of apparatus according to a second embodiment of the invention for electrically (FES) facilitated or assisted voluntary muscle contraction by means of voluntary EMG detected during the inter-pulse intervals of FES within the composite EMG which is overwhelmingly dominated by the m-wave by means of subtraction of the next m-wave model predicted and synthesized using a recursive self-adapting neutral network algorithm.

FIG. 8 shows one method by which the relatively tiny voluntary EMG signal can be detected within the composite signal totally dominated by the 1000 to 10,000 times bigger m-wave which swamps it during pulses of electrical stimulation of high enough intensity and close enough together, to maintain an effective muscle contraction. A recursive, autonomous, neural network, self-adapting algorithm which uses predictive modelling to progressively improve the subtraction of the m-wave from the composite signal, inter-pulse interval by successive inter-pulse interval as one succeeds the other, is used to help reveal the tiny voluntary-contraction electrical signal which can then be amplified and processed digitally to determine the amplitude and frequency content of this voluntary effort of the patient during the particular inter-pulse interval.

Several of the previous m-wave signals from the previous inter-pulse intervals are extracted from the composite and synthesised digitally to create the latest most up-to-date model of the next expected m-wave component. The weighting of the data from the most recent inter-pulse interval is higher with progressively less weight allocated to the least recent. The voluntary component of the composite signal is not in any fixed phase relationship with the very much larger (typically several hundred times) m-wave component and it consists of a wave shape which although it varies considerably every half cycle to succeeding half cycle, has a period of generally less than half that of the m-wave. For example, if the period of time between the first positive peak and subsequent negative is about 12 mS for the m-wave, the voluntary component will likely be roughly 4.5 mS. The recursive algorithm is thus able to sufficiently average out the tiny phase and amplitude variations in the composite signal by combining enough data from the several previous inter-pulse intervals.

This model is then subtracted in real time from the latest incoming m-wave in real time after each successive stimulation pulse. The recursive algorithm is able to statistically average out the tiny phase and amplitude "jitter" in the m-wave cause by the patient's voluntary effort (voluntary EMG component of the composite) by using this digital data from the last several inter-pulse intervals to create a sufficiently accurate digital model of the next expected inter-pulse interval (involuntary) m-wave component shape and amplitude. The error between what the next m-wave is thus expected to be and the actual m-wave detected is used to progressively optimise the process (self-learning).

It will therefore be apparent that the real time intensity of the voluntary effort as detected during useful electrically driven muscle stimulation (FES) can be used to proportionally control the intensity of that FES and thereby the moment to moment contraction force of the muscle itself. This therefore provides electrically facilitated useful muscle contraction in very weak patients and electrically assisted voluntary contraction in moderately weak patients.

FIG. 8 is a block diagram, is shown as one method of extracting the tiny voluntary EMG signal from the composite inter-pulse EMG waveform overwhelming dominated by the typically very much larger (2 to 3 orders of magnitude) m-wave and using this to control the amplitude of the next stimulation pulse in the on-going train of pulses necessary to produce and or sustain an effective muscle contraction. Weaker patients in need of such assistance may only be able to achieve a maximum voluntary EMG value of about 20 microvolts rms (0.00002 Volts RMS which is 0.020 millivolts) where as a typical maximal m-wave is about 10 my in amplitude.

This method predicts shape of the next m-wave component of the next inter-pulse composite EMG waveform from an on-going analysis of the most recent and subtracts a synthesised version of it from the incoming composite of the next inter-pulse interval to reveal the very much smaller Voluntary EMG component which is then amplified and processed to determine the amplitude of the next stimulation pulse. A recursive self-adapting algorithm uses the error between what it predicts and what it actually finds in the next inter-pulse interval to continually improve the accuracy of each synthesized model.

A micro-controller which has a built-in signal processor 501 communicates with a colour graphic touch screen display 503, key pad 502 and stimulation pulse generator 504. It includes analogue to digital convertors 501A and 501B and digital to analogue convertor 501C. It also controls an EMG/STIM selection switch 505 and a post pulse DC blocking and DC discharge block 506. Electrode connections can be switched between neuromuscular stimulation (STIM MODE) to transmit a pulse and EMG mode in which pulse transmission is inactive and electrode voltage is measured to permit electromyography (EMG). A composite EMG amplifier 507 is connected to the selection switch 505 through a post pulse discharge and DC blocking section 506. Active DC and common mode compensation is provided at 508 to drive a reference skin electrode. During every inter-pulse interval the composite EMG amplifier and filter 507 outputs the amplified signal to the low pass filter 509 which in turn provides its output to the analogue to digital input 501A where it is digitized and passed on to the signal processor in 501. The microcontroller/signal processor 501 performs analogue to digital conversion at 501a on the composite EMG wave during every inter-pulse interval at a rate of at least 4000 samples per second with a resolution of at least 16 bits and by means of a special recursive, self-learning algorithm compares each one with a model of the dominating m-wave component which it has predicted from statistical analysis of several of the most recent m-waves.

Starting at the beginning of every inter-pulse interval the controller/signal processor 501 outputs the predicted m-wave component by means of the digital to analogue convertor 501c and low pass filter 511 to a subtractor 510 where it is subtracted in real time from the incoming composite EMG waveform. The voluntary EMG component (typically 2 to 3 orders of magnitude smaller than the m-wave component of the composite) is output by the subtractor 510 to a voluntary EMG amplifier and filter 512. The amplified signal is then supplied to the analogue to digital converter 501b where it is digitised at a rate of at least 4000 samples per second with a resolution of at least 16 bit. The signal is then processed by the controller/signal processor 501 both to determine the remaining m-wave content caused by imperfections in the predicted m-wave model and the actual voluntary EMG (effort of muscle contraction). The m-wave error data is forwarded to the recursive, self-adapting algorithm to improve the accuracy of the synthesisation process for the next predicted m-wave and the amplitude of the voluntary effort to control the amplitude of the next stimulation pulse.

In use, the stimulation electrodes 24a, 24b are adhered to the skin above a specific muscle in the best position for good effect (knowledge of anatomy is helpful for this). The user is then asked to make their best efforts for a maximal contraction of the muscle during which time the EMG from these electrodes is measured such that the maximum and minimum reading of EMG readily achieved, is noted. The muscle is then stimulated via module 20 with these same electrodes to achieve a maximal comfortable contraction such that the device retains this value of stimulation current (mA). A maximum time for the stimulation may then be set e.g. to 5 seconds with an and the intervening period e.g. 10 seconds. The device is then switched to PECS stimulation mode and a start key is pressed. If the maximum comfortable stimulation current was found to be 30 mA, the minimum EMG achieved to be 4 microvolts and the maximum 15 microvolts, then in in proportional or PECS mode the device would function as follows. With the patient relaxed below 4 microvolts EMG there would be no stimulation. As the patient's voluntary contraction increased about 4 microvolts EMG the stimulation would start from zero mA linearly (or otherwise depending on the setting selected) such that at a level of 15 microvolts the maximum stimulation pulses of 30 mA would be achieved. As soon as the patient relaxed their voluntary contraction below 15 microvolts the stimulation would (immediately) proportionally reduce until it stopped altogether when they relaxed to below 4 microvolts. Or, if the time of the stimulation reached 5 seconds the stimulation would stop and the 10 seconds pre-set rest period would begin. During this rest period, any contraction above 4 microvolts would not result in stimulation in order to prevent over stimulation. PECS would only be re-enabled at the end to the rest period. In this way, the signals in the motor neurones of the user are complemented by a powerful stimulation signal which is proportional to EMG signal level above the pre-set threshold, and the patient is given a sensation of full muscular control rather than a mechanical-seeming on/off signal. It is believed that the resulting sensations of control will enhance the learning process needed for recovery or increased muscle power, and both recovery/enhancement time will be reduced and the extent of recovery/enhancement will be increased.

In the above embodiments the amplitude of the next pulse of NMES stimulation would be directly proportional to the average value of EMG detected between each pulse as follows:

mA=interpulse EMG value−2×threshold value/maximum EMG level obtained in the set up stage× the maximum mA require to give an acceptable maximal but still comfortable contraction For example, if:

A: EMG values determined in the EMG only part of the set-up stage. If the stable "Rest EMG" was found to be 2 µV and the maximum reliably-repeatable voluntary contraction was found to be 10 µV B: Maximum comfortable mA found during the NMES only part of the set up stage with a predetermined stimulation pulse width and pulse repetition rate selected by the therapist 40 mA Then the mA value of the next pulse in the pulse train could be calculated as follows:— mA=40×(interpulse EMG µV−4)/10

Up to 4 µV there would be no stimulation. At 10 µV or above (if such were to occur) it would be 40 mA. At 6 µV it would be 13.3 mA, at 7 microvolts it would be 20 mA and so on. While the user held a steady voluntary contraction during this stimulation, the stimulation current would stay the same. The length of a therapy session could be pre-set so that after, for example, about 2 minutes the mA would automatically ramp down, if it happened to be up, and the session ended. The system could also detect signs of muscle fatigue from a progressive lowering in the average frequency of the EMG and or other properties and this could be also be used to end the session.

The above procedure could be readily elaborated on for multichannel systems moderated with extra MEMS sensors and or automated visual control to engage the plasticity of the nervous system to perform a range of very important specific physical functions with increasing independence.

Although a linear relationship between EMG and STIM pulse amplitude has been described, other types of relationship may be used, e.g. STIM pulse amplitude which increases exponentially with increasing EMG signal. It will be appreciated that in this embodiment it may be advantageous to configure the system so that notwithstanding the exponential relationship the STIM pulses do not exceed a maximum amplitude even on prolonged high values of the EMG signal.

Various modifications may be made to the embodiment described above without departing from the invention. For example, instead of a single pair of electrodes and a reference electrode, there could as previously explained be added a second pair of electrodes so that one pair is used during STIM while the other pair is used for EMG. Instead of providing analog subtractor 510 the voluntary component of the EMG signal could be derived digitally.

The invention claimed is:

1. Apparatus for neuromuscular stimulation, comprising:
   (a) a module configured to supply a succession of symmetrical bipolar square-wave stimulation (STIM) pulses having a phase duration which is short compared to the inter-pulse interval;
   (b) a module for receiving EMG signals from skin adjacent a muscle whose contraction is to be stimulated, which module is configured to operate substantially continuously between each pair of successive pulses; and
   (c) a controller configured to:
   1) cause the EMG-receiving module to be operable during quiescent periods between successive pulses to receive composite signals that comprise: m-waves of frequency similar to that of the stimulation pulses and of amplitude up to 10 mV, and a voluntary component having a frequency higher than that of the m-waves and an amplitude 2-3 orders of magnitude less than that of the m-waves;
   2) create a predicted m-wave component for the next inter-pulse interval from a digital model of the next expected inter-pulse interval m-wave component shape and amplitude using digital data from the last several inter-pulse intervals and a recursive algorithm for statistically averaging out a phase and amplitude jitter in the m-wave caused by voluntary effort;
   3) output the predicted m-wave component at the beginning of the next inter-pulse interval to a subtractor configured to subtract the predicted m-wave component in real time from the incoming composite EMG waveform, thereby obtaining a subtracted signal;
   4) amplify and digitize the subtracted signal;
   5) process the amplified and digitized subtracted signal to determine the remaining m-wave content caused by imperfections in the predicted m-wave model and to determine the actual voluntary EMG;
   6) forward the m-wave error data to a recursive, self-adapting algorithm to improve the accuracy of the synthetization process for the next predicted m-wave; and
   7) control the amplitude of the next stimulation pulse using the determined actual voluntary EMG.

2. The apparatus of claim 1, wherein the controller is configured to output the value of the determined actual voluntary EMG signals above a predetermined threshold.

3. The apparatus of claim 1, wherein the controller is configured to average the detected voluntary EMG signals to smooth amplitude modulation, whereby a user can achieve smooth muscle contraction.

4. The apparatus of claim 1, wherein the controller is configured so that the STIM pulses do not exceed a maximum amplitude even on prolonged high values of the voluntary EMG signal.

5. The apparatus of claim 1, including circuits configured to reduce DC voltage at the electrodes during the inter-pulse interval and avoid swamping of the composite EMG signal.

6. The apparatus of claim 1, wherein the controller is configured:
   to detect the voluntary component by averaging detected m-wave pulses in periods between successive stimulation pulses to derive predicted m-wave profiles; and
   for successive m-waves, to determine differences between detected and predicted m-wave values of period less than that of the m-wave and corresponding to said voluntary component.

7. The apparatus of claim 1, wherein the EMG-receiving module is configured to sample the EMG signals at a frequency of 1-2.5 kHz.

8. The apparatus of claim 1, comprising skin electrodes configured to receive the EMG signals and supply the STIM pulses.

9. The apparatus of claim 1, configured for use with a subject who is a stroke or paresis patient or who is a patient suffering from cerebral palsy, incontinence, or muscle atrophy.

10. The apparatus of claim 1, configured to operate in a sports clinical mode for promoting muscle growth and endurance.

11. The apparatus of claim 1, wherein the controller is configured to provide modulation in real time while supplying stimulation pulses, whereby the subject is given a sensation of natural muscle control and/or the possibility for greater precision of neuromuscular control.

12. A method for supplying neuromuscular stimulation to a subject, comprising:
   (a) supplying a succession of symmetrical bipolar square-wave stimulation (STIM) pulses having a phase duration which is short compared to the inter-pulse interval;
   (b) receiving EMG signals from skin adjacent a muscle whose contraction is to be stimulated at an EMG-receiving module substantially continuously in quiescent periods between each pair of successive STIM pulses, the received EMG signals being composite signals that comprise 1) m-waves of frequency similar to that of the stimulation pulses and an amplitude up to 10 mV, and 2) a voluntary component having a frequency higher than that of the m-waves and an amplitude 2-3 orders of magnitude less than that of the m-waves;
   (c) creating a predicted m-wave component for the next inter-pulse interval from a digital model of the next expected inter-pulse interval m-wave component shape and amplitude using digital data from the last several inter-pulse intervals and a recursive algorithm for statistically averaging out a phase and amplitude jitter in the m-wave caused by voluntary effort;
   (d) outputting the predicted m-wave component at the beginning of the next inter-pulse interval to a subtractor configured to subtract the predicted m-wave component in real time from the incoming composite EMG waveform;
   (e) amplifying and digitizing the subtracted signal;
   (f) processing the amplified and digitized subtracted signal to determine the remaining m-wave content caused by imperfections in the predicted m-wave model and determine the actual voluntary EMG;
   (g) forwarding the m-wave error data to a recursive, self-adapting algorithm to improve the accuracy of the synthetization process for the next predicted m-wave; and
   (h) controlling the amplitude of the next stimulation pulse using the determined actual voluntary EMG.

13. The method of claim 12, wherein the EMG-receiving module detects the voluntary component by averaging detected m-wave pulses in periods between successive stimulation pulses to derive predicted m-wave profiles; and, for successive m-waves, determines differences between detected and predicted m-wave values of period less than that of the m-wave and corresponding to said voluntary component.

14. The method of claim 13, wherein the EMG-receiving module samples the EMG signals at a frequency of 1-2.5 kHz.

15. The method of claim 12, wherein the EMG-receiving module outputs the value of the voluntary EMG signals above a predetermined threshold, operates substantially continuously between each pair of successive pulses and averages the detected voluntary EMG signals to smooth amplitude modulation, whereby a user can achieve smooth muscle contraction.

* * * * *